United States Patent [19]
Magnuson et al.

[11] Patent Number: 5,592,083
[45] Date of Patent: Jan. 7, 1997

[54] SYSTEM AND METHOD FOR CONTRABAND DETECTION USING NUCLEAR QUADRUPOLE RESONANCE INCLUDING A SHEET COIL AND RF SHIELDING VIA WAVEGUIDE BELOW CUTOFF

[75] Inventors: Erik E. Magnuson, Escondido; Charles R. Moeller, Cardiff; Julian D. Shaw, Guerneville; Alan G. Sheldon, San Diego, all of Calif.

[73] Assignee: Quantum Magnetics, Inc., San Diego, Calif.

[21] Appl. No.: 400,679

[22] Filed: Mar. 8, 1995

[51] Int. Cl.$^6$ .............................. G01V 3/08; G01V 3/10
[52] U.S. Cl. ............................ 324/300; 324/318
[58] Field of Search ...................... 324/300, 307, 324/309, 318, 321, 322, 310, 313, 316

[56] References Cited

U.S. PATENT DOCUMENTS

| | | | |
|---|---|---|---|
| 4,166,972 | 9/1979 | King et al. | 324/0.5 AC |
| 4,296,378 | 10/1981 | King | 324/313 |
| 4,514,691 | 4/1985 | De Los Santos et al. | 324/301 |
| 4,769,602 | 9/1988 | Vinegar et al. | 324/303 |
| 4,887,034 | 12/1989 | Smith | 324/307 |
| 5,159,617 | 10/1992 | King et al. | 324/307 X |
| 5,159,929 | 11/1992 | Morris et al. | 324/318 |
| 5,206,592 | 4/1993 | Buess et al. | 324/307 |
| 5,233,300 | 8/1993 | Buess et al. | 324/307 |
| 5,243,282 | 9/1993 | Miller | 324/300 |
| 5,365,171 | 11/1994 | Buess et al. | 324/307 |

OTHER PUBLICATIONS

Klainer et al., *Fourier Transform Nuclear Quadrupole Resonance Spectroscopy*, Fourier, Hadamard & Hilbert Transforms In Chemistry, Plenum Press, pp. 147–182 (1982).

Shaw, *Narcotics Detection Using Nuclear Quadrupole Resonance (NQR)*, Proc. First Int'l. Symp. on Contraband and Cargo Inspection Tech., pp. 333–341 (1992).

Buess et al., *Explosives Detection by $^{14}N$ Pure NQR*, Advances in Analysis and Detection of Explosives, pp. 361–368 (1993).

Noble, *NQR For Bomb Detection*, Analytical Chemistry, vol. 66, No. 5, pp. 320–324 (1 Mar. 1994).

Rollwitz et al., *Fundamentals of Nuclear Magnetic Resonance . . . Explosives*, Proc. New Concepts Symp. & Workshop on Det. & Ident. of Explosives, NTIS, pp. 377–389 (1978).

King et al., *Appln. of Nuclear Magnetic . . . Explosives*, Proc. New Concepts Symp. & Workshop on Det. & Ident. of Explosives, NTIS, pp. 391–398 (1978).

Marino, *Detection and Identification of Explosives by $^{14}N$ NQR*, Proc. New Concepts Symp. & Workshop on Det. & Ident. of Explosives, NTIS, pp. 399–403 (1978).

*Primary Examiner*—Sandra L. O'Shea
*Assistant Examiner*—Roger C. Phillips
*Attorney, Agent, or Firm*—Baker, Maxham, Jester & Meador

[57] ABSTRACT

A system for detecting a target substance within a class of explosives and narcotics containing quadrupolar nuclei through the use of nuclear quadrupole resonance (NQR). The system applies an RF signal to a coil to excite the substance under test. If the target material is present, an NQR signal will be picked up by the same coil. That signal is compared with known NQR signals in frequency and amplitude. A signal is displayed in an appropriate way if a threshold value of the NQR signal is equalled or exceeded. The coil is tuned by means of an auto-tune feature. Effective RFI shielding is provided to prevent external contaminating signals from being detected by the coil and to prevent RF signals from escaping from the scanner. The invention also includes the method for performing tests with the system.

19 Claims, 5 Drawing Sheets

SYSTEM AND METHOD FOR CONTRABAND DETECTION USING NUCLEAR QUADRUPOLE RESONANCE INCLUDING A SHEET COIL AND RF SHIELDING VIA WAVEGUIDE BELOW CUTOFF

BACKGROUND

1. Field of the Invention

This invention relates generally to a bulk substance detection system for detecting concealed explosives and narcotics, and more particularly to a practical system and method for such contraband detection employing nuclear quadrupole resonance (NQR).

2. Discussion of the Related Art

Earlier work in detecting contraband substances centered on the subject of nuclear magnetic resonance (NMR). Work in this area is reflected in U.S. Pat. Nos. 4,166,972, 4,296, 378 and 4,514,691. A drawback of NMR is that is requires relatively large magnets. Magnets are relatively expensive, would likely cause personnel to be exposed to large static magnetic fields, and could damage magnetically recorded material.

Another attempt at explosives detection employed thermal neutron analysis (TNA), which can detect nitrogen in any form. Although it could detect explosives, it was also triggered by nitrogen-rich nylon and wool, and other innocuous items. These shortcomings resulted in a high rate of false positives. Because it employed potentially hazardous radioactive emissions, TNA systems were also required to be heavily shielded. As a consequence, TNA systems were very large, very expensive, and also produced a high rate of false positives.

X-ray screening, commonly used in airports, does not have the same overall limitations as TNA. However, it cannot alert the operator to the presence of explosives or drugs, much less identify them. X-ray screening can only "see images that the operator must interpret quickly." Further, X-ray screening emits potentially hazardous ionizing radiation.

With respect to explosives, plastic explosives such as C-4 and Semtex, containing RDX and PETN, have an almost infinite variety of possible shapes and uses for terrorist bombing tactics. Plastic explosives are highly stable, have clay-like malleability and are deadly in relatively small quantities. A small piece of plastic explosive, a detonator, and a trip wire inside a large mailing envelope can cause a deadly explosion. Unfortunately, without close—and potentially dangerous—visual inspection, plastic explosives can be made virtually untraceable. Because of the drawbacks of TNA, NMR and X-ray, as mentioned above, they have generally proven ineffective for practical bulk detection of these types of explosives. In particular, detection of sheet explosives, typically having a thickness as small as one-quarter inch, has not been effectively accomplished by prior technologies.

The wide-scale attempts to fight the illegal drug trade indicates that narcotics detection is also extremely important. The need for a simple procedure for detecting drugs inside sealed containers, mail parcels, and other small packages, quickly and accurately, is immeasurable. Conventional detection methods are time-consuming, costly, and have only marginal reliability at best.

NQR is a branch of radio frequency spectroscopy that exploits the inherent electrical properties of atomic nuclei. Nuclei with non-spherical electric charge distributions possess electric quadrupole moments. Quadrupole resonance arises from the interaction of the nuclear quadrupole moment of the nucleus with the local applied electrical field gradients produced by the surrounding atomic environment.

Any chemical element's nucleus which has a spin quantum number greater than one half can exhibit quadrupolar resonance. Many substances (approximately 10,000) have been identified that exhibit quadrupolar resonance, among such nuclei being: $^7$Li, $^9$Be, $^{14}$N, $^{17}$O, $^{23}$Na, $^{27}$Al, $^{35}$Cl, $^{37}$Cl, $^{39}$K, $^{55}$Mn, $^{75}$As, $^{79}$Br, $^{81}$Br, $^{127}$I, $^{197}$Au, and $^{209}$Bi. It so happens that some of these quadrupolar nuclei are present in explosive and narcotic materials, among them being nitrogen ($^{14}$N), chlorine ($^{35}$Cl, $^{37}$Cl), oxygen ($^{17}$O), sodium ($^{23}$Na), and potassium ($^{39}$K). The most studied quadrupole nucleus for explosives and narcotics detection is nitrogen.

In solid materials, electrons and atomic nuclei produce electric field gradients. These gradients modify the energy levels of any quadrupolar nuclei, and hence their characteristic transition frequencies. Measurements of these frequencies or relaxation time constants, or both, can indicate not only which nuclei are present but also their chemical environment.

When an atomic quadrupolar nucleus is within an electric field gradient, variations in the local field associated with the field gradient affect different parts of the nucleus in different ways. The combined forces of these fields cause the quadrupole to experience a torque, which causes it to precess about the electric field gradient. Precessional motion generates an oscillating nuclear magnetic moment. An externally applied radio frequency (RF) magnetic field in phase with the quadrupole's precessional frequency can tip the orientation of the nucleus momentarily. The energy levels are briefly not in equilibrium, and immediately begin to return to equilibrium. As the nuclei return, they produce an RF signal, known as the free induction decay (FID). A pick-up coil detects the signal, which is subsequently amplified by a sensitive receiver to measure its characteristics.

One distinguishing feature of an NQR response is its precessional frequency. Two independent factors determine the precessional frequency: the quadrupolar nucleus, and its local crystalline environment. There may be one or more characteristic NQR frequencies for each substance containing quadrupolar nuclei.

The second distinguishing features are the NQR relaxation times. Relaxation times are a measure of the nuclei's rate of return to the equilibrium state following disturbance by an RF pulse. Relaxation times are compound-, temperature-, and pressure-specific. Relaxation times also determine the repetition rate and timing of RF pulses required for exciting and detecting a specific NQR signal. Relaxation times can be as short as a few hundred microseconds or as long as several seconds.

Detection of NQR signals normally requires RF transmitting and receiving apparatus. To minimize noise and radio frequency power requirements and improve receiver sensitivities, conventional NQR systems use a narrow band (high Q) sample coil in both the transmitting and receiving equipment. Even so, several factors can significantly degrade the effectiveness of detecting NQR signals. Among these factors are: (1) the presence of conductive materials inside the sample coil; (2) the presence of materials with a high dielectric constant inside the sample coil; (3) temperature, which can affect the value of the capacitance used for tuning and matching the RF coil; and (4) mechanical movement of the coil which respect to its surroundings. All of these factors can cause serious de-tuning of the detection apparatus, which in turn, lowers the detection sensitivity of the coil. Accordingly, NQR systems have largely been limited to small sample laboratory systems with little or no "real-world" potential.

The NQR energy level transitions are observed primarily in the radio frequency range. Detection of these transitions requires an RF source to excite the transition, and an RF receiving mechanism to detect the signals returning from the nuclei. Normally, the signals appear at a pre-defined frequency. An RF coil tuned to, or close to, that predefined frequency can excite and/or detect those signals. The signals are of very low intensity and can only be observed for a short time, approximately 10 μs to 10 ms. As a consequence, there is a need for an NQR receiver that can be tuned to a (usually) high Q, has very low noise, and is capable of fast recovery after a high-voltage RF pulse.

Previous work in this area is reflected in U.S. Pat. Nos. 4,887,034, 5,206,592, 5,233,300 and 5,365,171. Use of NQR for explosives and narcotics detection is also discussed in Buess et al., Explosives Detection By $^{14}$N Pure NQR, *Advances in Analysis and Detection of Explosives* (J. Yinon (ed.)) pp. 361–368 (1993), and Shaw, *Narcotics Detection Using Nuclear Quadrupole Resonance (NQR)*, Contraband and Cargo Inspection Technology International Symposium, Washington, D.C., pp 333–341 (1992).

Detection by means of NQR is possible for both explosives and narcotics, partially because they have as a constituent element $^{14}$N in crystalline form. Particularly with respect to narcotics, this is true of cocaine base, cocaine hydrochloride and heroin based narcotics. The hydrochloride forms of narcotics, such as cocaine hydrochloride, also contain quadrupolar nuclei $^{35}$Cl and $^{37}$Cl.

A significant factor in contraband detection by means of NQR is that quadrupolar nuclei that are commonly present, and potentially readily observable, in narcotics and explosives include nitrogen ($^{14}$N) and chlorine ($^{35}$Cl and $^{37}$Cl), among other possible nuclei. Thus, in commercial applications it is necessary to be able to detect quadrupolar nuclei contained within articles of mail, mail bags or airline baggage, including carry-on and checked luggage. While the resonant frequencies of the nitrogen in these substances differs for each chemical structure, these resonant frequencies are well defined and consistent. By applying an RF signal to a container having any of these suspected substances inside, and then detecting any quadrupolar resonance thus engendered by the application of RF pulses, the identity of the contraband substance can be easily determined.

SUMMARY OF THE INVENTION

Broadly speaking, this invention provides a practical nuclear quadrupole resonance (NQR) detector system for improved bulk contraband detection. More specifically, the invention employs the principle of NQR to simply and relatively inexpensively, with a very low rate of false alarms, detect the presence of explosives and/or narcotic materials within closed or sealed packages or within baggage having many other articles of other materials contained therein. It is particularly effective in detecting contraband materials in sheet form, which are as thin as one quarter inch or possibly even thinner.

The invention provides a commercially practical system employing the known properties of the substances and the known principles of NQR to detect and identify contraband products which may be hidden inside airline baggage or concealed in a variety of packaging. RF pulses are applied to an RF coil in which the specimen resides for purposes of the test. An appropriately formed RF shield prevents stray signals from entering or leaving the cavity in the coil so that the test results can be reliable and external RF radiation is insignificant. Because insertion of the sample in the RF coil causes de-tuning, an automatic tuning system is provided to re-tune the RF coil to provide optimum performance under a range of coil loading conditions. This tuning system also corrects for the possible degradation of NQR response signals caused by temperature changes and others of the factors set out above in the Background.

An analog signal is converted to digital form and is sent to a digital signal processor. The digitized signal is digitally filtered and compared with a predetermined threshold level. Alternatively, once the signal is apodized and Fourier transformed, it occurs as a quadrature "spike" at or close to 0 Hz in the frequency spectrum, and is then filtered and compared to the known signal of the material to be detected. The signal from a digital signal processor is applied to a display device which indicates whether the package is clean, has contraband, or needs further inspection.

In a practical system, the presence of other conductive material in the package being inspected may cause acoustic ringing as a result of the applied RF pulses. The system of the invention has provisions to filter out such acoustic ringing when it occurs so that the NQR signal is isolated and is not hidden in the ringing signal.

BRIEF DESCRIPTION OF THE DRAWING

The objects, advantages and features of this invention will become readily apparent from the detailed description, when read in conjunction with the accompanying drawing, in which.

DETAILED DESCRIPTION OF THE PREFERRED EMBODIMENTS

NQR is a linear spectroscopy, that is, the signal strength is directly proportional to the quantity of contraband material containing quadrupolar nuclei. Because the NQR frequencies of different compounds are quite distinct, the system of this invention does not encounter false alarms from the NQR signals of other benign materials. For example, $^{14}$N NQR absorption frequencies from crystalline materials are virtually unique. When looking for the nitrogen signal at the NQR frequency of RDX, for example, only nitrogen in RDX will be detected. If other compounds containing $^{14}$N are in the same parcel as the RDX, those other compounds would not be identified. The frequency resulting from NQR in a target substance will be sharply defined, while other $^{14}$N-containing substances would not provide a sharp peak NQR response. Another factor of importance is that NQR is a bulk detector, that is, sheet, bulk or distributed materials are equally detected.

The unique NQR resonance frequencies of a large number of compounds have been identified and recorded. The frequency information is stored in a memory in the system of the invention and provides a database for comparison of detected signals. For general reference purposes, the NQR frequencies of quadrupolar nuclei are generally within the range of 0.5 MHz to 5 MHz.

It is important to understand that explosives and narcotics have "fingerprints" that are different from innocuous substances. To thwart analysis by NQR, it would require the impossible task of altering the chemical structure of the contraband, and the laws of nature cannot be altered. Thus, to change a substance so that the elements of interest in the particular contraband could not be detected by means of NQR would require changing the chemical composition and make it other than the contraband itself.

Figure 1:
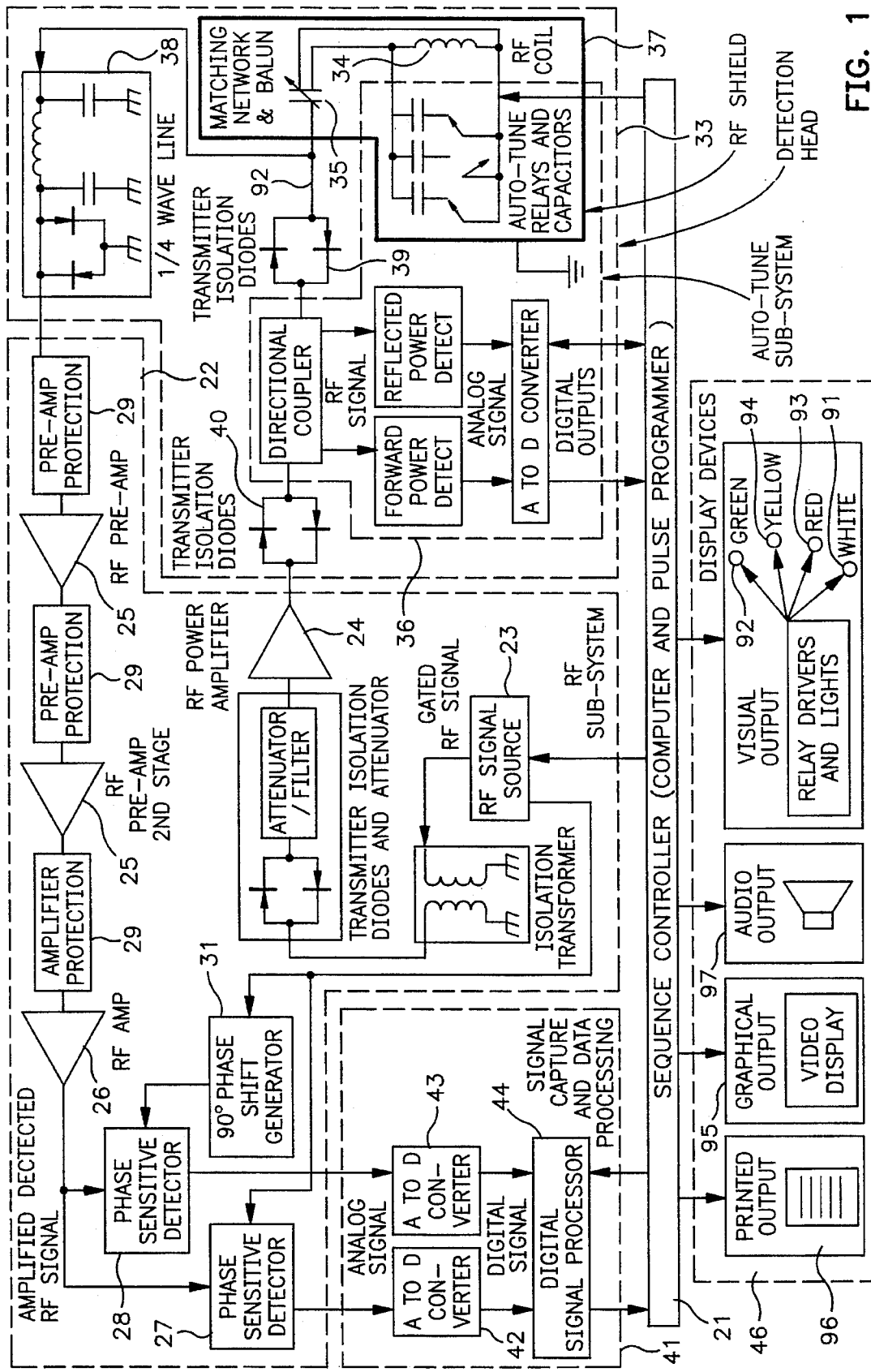
FIG. 1 is a block diagram of the basic system of the invention.

With reference now to the drawing, and more particularly to FIG. 1 which shows the system, block 21 is the sequence controller subsystem. This subsystem provides precise timing and other control functions for all other elements and subsystems of the invention. It generally would comprise a microprocessor-based device which provides means to download and initialize the sequence control information to all other subsystems, and would include appropriate data storage or memory means. It also stores information on the results of individual scans for future reference. As one specific embodiment, the microprocessor based control and storage device may be a personal computer (PC) with a hard disk.

The sequence controller subsystem also includes a pulse programmer which is a high-precision, high-resolution device that runs off the standard computer bus. The pulse programmer provides the precise sequence control required for correct operation of all other major components in the NQR scanner of the invention. In combination with the personal computer, it also provides the precisely defined pulses and triggers to activate the subsystems to which it is connected and which will be discussed in detail below.

Radio frequency (RF) subsystem 22 has several functional elements including RF signal source 23, RF power amplifier 24, receiver RF preamplifiers 25, receiver RF amplifier 26 and detectors 27 and 28. The detectors are here shown as phase-sensitive detectors. A 90° degree phase shift generator 31 is also part of the RF subsystem. This is one embodiment of the invention and is used when detectors 27 and 28 are phase shift detectors. Other types of detectors could be employed and the phase shift generator would not be required. Conventional amplifier protection devices 29 are also part of the RF subsystem. They are typical RF amplifier-related elements and need not be described in detail here.

RF signal source 23 provides either continuous or pulsed RF excitation at a frequency corresponding to the resonant frequency of the sample material. For example, RDX-based plastic explosives have a resonant frequency of approximately 3.410 MHz while PETN-based plastic explosives have a resonant frequency of approximately 890 KHz. The excitation source is fed into amplifier 24 of sufficient power rating to generate about 1 gauss of RF magnetic field within the coil. The excitation frequency need not be exactly the same as the target substance NQR frequency but it should be within about 500–1000 Hz. The RF excitation for NQR detection could be a single pulse of 10 μs–500 μs duration, depending on the substance being tested for. Such a single pulse could cause an NQR return, but the nuclei may not have reached a steady state of precess so the NQR return might not be sufficiently strong to be detectable or useful. For a letter bomb scanner, approximately three seconds of RF pulses at a repetition rate of 667 pulses per second, meaning a train of 2000 pulses having a pulse width of 200 μs each, would preferably be applied. The pulse repetition rate can range between 300 Hz and 2 KHz. This would result in a series of NQR signals which are added and averaged in digital signal processor 44. This is an application of the conventional technique where target signals are added linearly while noise adds randomly, thereby building a clearly definable pulse by improving the signal-to-noise ratio (SNR). Any method to improve SNR might advantageously be used.

The power requirements of the invention are generally proportional to the detection coil volume. An explosives scanner for mail packages with a 25 liter detector coil volume might have an RF power amplifier rated at about 25 Watts, peak value, for example. The amplifier produces a uniform RF field of about 1 gauss over the entire 25-liter volume. In other applications, such as in narcotics detection, the RF field may be greater than this value. For airline baggage, an explosives detection head of about 300 liters (10 ft$^3$) volume within the coil requires a 1 to 2 KW RF power amplifier. These parameters are provided for reference purposes and are not meant to define or limit the actual characteristics of a practical NQR system.

The RF excitation pulses are fed from amplifier 24 into detection head 33, the operation of which will be discussed below. After the sample in the detection head has been excited by the RF pulse, a short RF coil "ring-down" or dead time occurs, during which the receiver is "deaf," before sensing occurs. This ring-down time could, for example, be 500 μs. Then RF coil 34 detects the NQR signals and the response is amplified by low-noise, high-gain preamplifiers 25 having a gain of 20 to 30 dB, and a noise figure of 1 to 2 dB. Examples of such preamplifiers are Anzac Model AM-110 and Mini-Circuits Model ZFL-500 LNS.

In the package or letter scanner size configuration of the invention, after the received signal has been sufficiently amplified by RF amplifiers 25 which, together with amplifier protection components 29, include appropriate conventional filter functions, the received signal is fed into two phase sensitive detectors 27 and 28, having reference signals shifted 90° from each other by means of phase shift element 31. Note that reference RF signal from RF source 23 is applied to phase sensitive detector 27 while the reference signal to phase sensitive detector 28 passes through phase shift element 31. The two mutually phase-shifted analog signals are then fed into signal-capture and data processing subsystem 41, which will be discussed below.

Detection head subsystem 33 is comprised of four main components. These are RF coil 34, an RF probe circuit which is RF tuning and matching network 35, auto-tune subsystem 36 and RF shield 37. The detection head serves two primary purposes. One is to produce a homogeneous RF field in the RF coil. The other is to receive the raw NQR signal, if present, from the item under investigation.

RF coil 34, which may also referred to as an antenna, is made of a highly conductive material, such as copper. The conductor should have a thickness in the order of at least five times the skin depth of the material of the conductor at the operational frequency. This ensures a minimal amount of resistance to the flow of current when the coil is energized with RF. A 25 liter detection volume (for a mail scanning device) has a single turn, high-Q, 0.010 inch-thick copper coil made of a single sheet. The skin depth of copper at 3.4 MHz is about 0.001 inches and the skin depth of copper at 900 KHz is about 0.002 inches. Direct coil tuning results in an increased overall efficiency for the mail scanning embodiment of the invention. The single-turn, high-Q coil, when no sample is present, that is, the coil is empty, requires approximately 30,000 pF of capacitance for tuning at about 3.4 MHz in order to detect the $^{14}$N resonant frequency of RDX explosives. Using a series of switches to add or remove capacitance in order to re-tune the coil under differing load conditions, it has been determined that it would be useful for the system to be re-tunable for a 10% change in tuning capacitance. In this particular application, the coarse tuning increments in capacitance were selected to be approximately 80 pF, and in the fine tuning mode, 10 pF. The RF signal source and amplifier (23, 24) of RF subsystem 22 used to exercise the auto-tune subsystem are the same as those used to excite the RF coil for substance detection purposes. Details of the auto-tune subsystem follow.

AUTO-TUNE SUBSYSTEM

Figure 5:
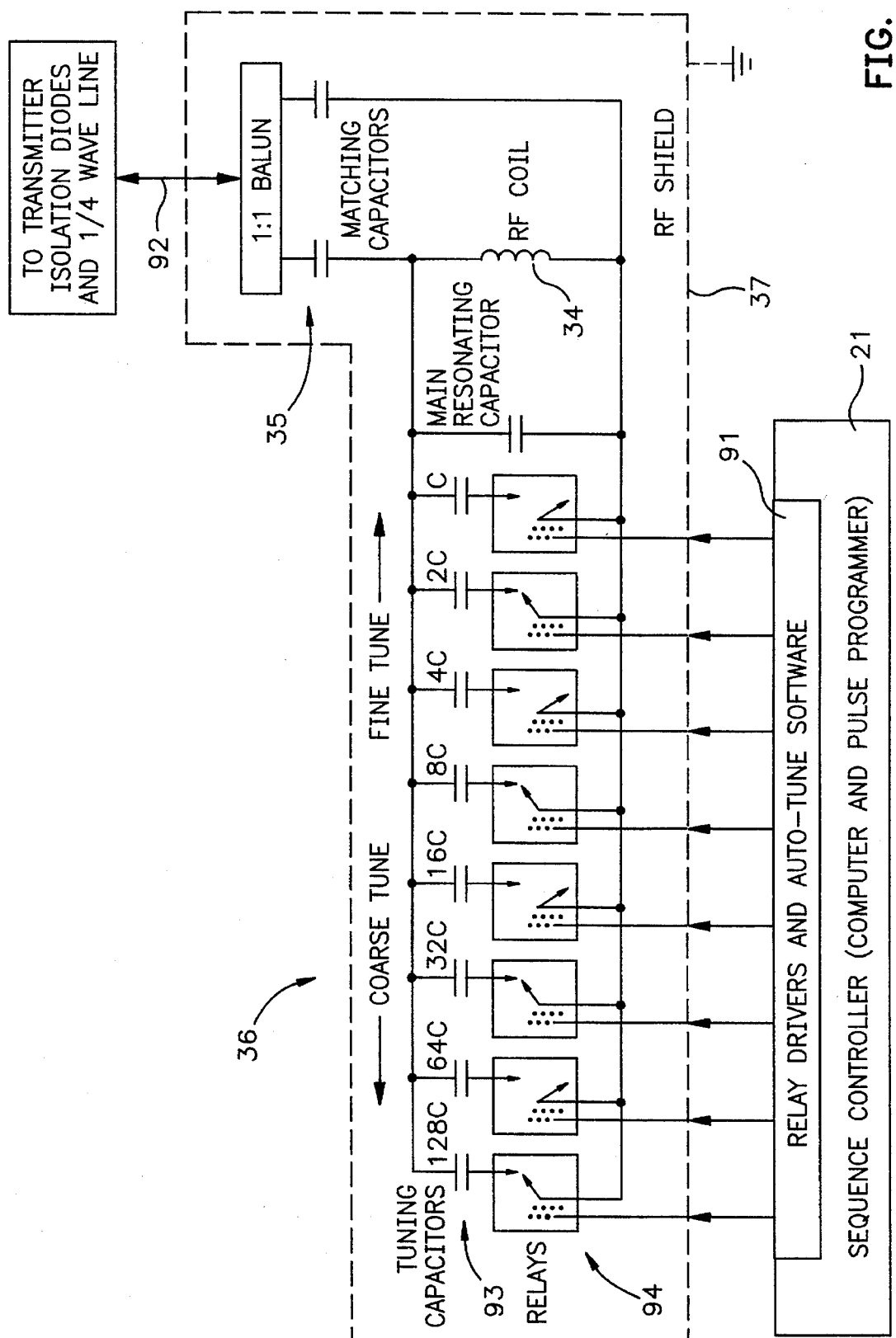
FIG. 5 shows the auto-tune subsystem in greater schematic detail.

Apparatus for automatic fine tuning of the NQR detection coil/head under adverse conditions is shown in FIG. 5. Within sequence controller 21 is software or control programming 91 for auto-tune subsystem 36. The auto-tune subsystem is preferably incorporated within RF shield 37, as are RF coil 34 and matching network 35. Input/output line 92 connects the tuned RF coil to the amplified RF excitation signal and connects the coil as the receiver of the NQR signals to ¼ wave line 38 (FIG. 1).

The system consists of a series of fixed value capacitors 93 switched by an equal number of vacuum relays 94. The amount of capacitance switched into the tuning circuit is determined by measuring the amount of power being transferred from RF amplifier 24 to RF detector coil 34 (or, more precisely, the amount of "forward" to "reflected" power.) The means to measure this power transfer efficiency consist of a variety of common RF techniques. For one application, a directional watt meter is used to measure the amount of "forward" to "reflected" power. Based on the power transfer efficiency, capacitors are switched in or out of the circuit to maximize power transfer efficiency from the RF amplifier to the RF coil. The system is thus re-tuned to provide the most efficient and most sensitive RF coil. Once the state of tune of the RF coil has been determined by the values of the forward and reflected power, the coil is re-tuned by switching in capacitance according to the algorithm described below.

Figure 6:
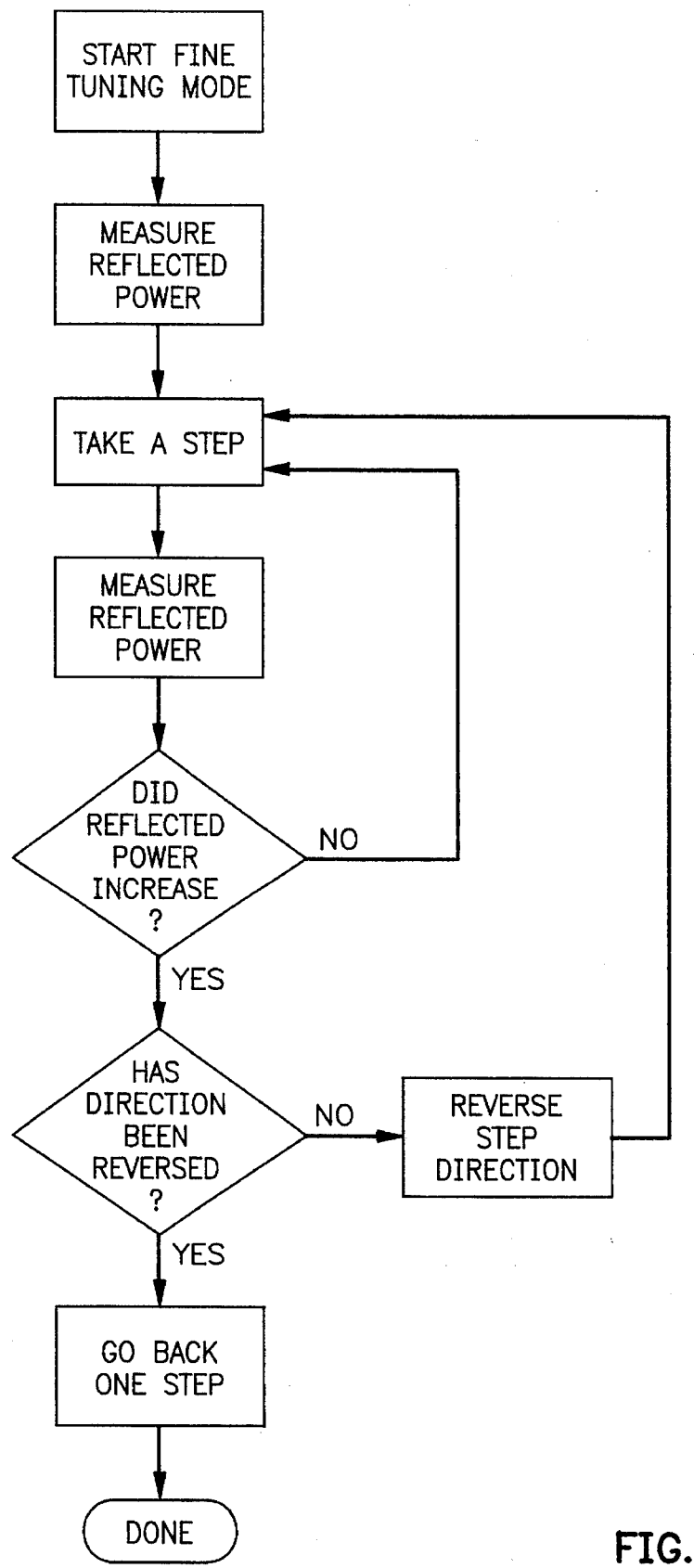
FIG. 6 is a flow diagram of the operation of the auto-tune subsystem of FIG. 5.

Tuning of the RF coil consists of two stages: coarse tuning and fine tuning. A flow diagram for the sequence is shown in FIG. 6. The value of "C" in FIG. 5 has been chosen to be 10 pf, so each capacitor is a multiple of "C." Other values could be assigned as desired.

Coarse Tuning

Both the forward and reflected power are measured. If reflected power is greater than a predefined percentage of forward power, then the system self-adjusts to coarse tuning by making the large jumps mentioned above (by increasing capacitance until reflected power drops below the maximum value of reflected power that the fine tuning mode can handle). When that condition is reached, then the system goes into fine tuning. The upper limit of the size of the capacitance jump is determined by the capacitance range of the fine tuning subsystem. When the reflected power drops below a preset upper size limit, then the system will begin fine tuning. This is the "start fine tuning mode" point.

Fine Tuning

After taking a step (either increasing or decreasing capacitance) the reflected power is measured again. If reflected power has increased and the direction (i.e., increase or decrease of capacitance) has been reversed from the previous step, then the system goes back one step to the "start fine tuning mode" point. Fine tuning begins again, only this time in the opposite direction (that is, adding capacitance instead of subtracting it). If, however, the reflected power did not increase, then another step is taken in the same direction (adding or subtracting capacitance). This process continues until another reversal of the direction is encountered. At this stage the system goes back one step and the fine tuning is complete. The reflected power is now at a minimum. The forward power is measured and compared to a pre-defined value, to ensure correct functioning of the RF transmitter.

Auto-tune subsystem 36 performs two major functions. One is to re-tune the RF coil to provide optimum performance under a range of coil loading conditions. Secondly, it determines the state of the tune by comparing it to a pre-defined "zero" setting. The system consists of a radio frequency power source, a directional watt-meter and switched capacitors to vary tuning reactance. Control unit 21 operates the RF power source, measures the reflected power and then varies the tuning reactance until a minimum in reflected power is reached. The system's ability to tune the sample coil directly results in increased overall efficiency. Antenna tuning systems commonly used in radio electronics are unnecessarily complex for coil fine tuning in NQR applications. They also have certain inefficiencies for NQR applications: they cannot tune the coil directly, and they experience higher feed line losses, which can contribute to noise. Furthermore, antenna tuning systems tend to be too general in terms of what is being matched (for example, tuning range).

RF probe 35 is a matching network and Balun which provides tuning and matching of the coil, and also protects preamplifiers 25 from the high voltages in the coil during RF excitation. RF probe 35 matches RF coil 34 to a 50 Ω unbalanced input. This makes the coil look like a 50 Ω transmitter/receiver and is conventional matching technology. The function of ¼ wave line 38 is to isolate the receiver from the transmitter. Transmitter isolation diodes 39 and 40 have a related function. The auto-tune subsystem determines the state of the tune of RF coil 34 in the detector head by matching the RF coil to its load in the detection volume. It measures the amount of power transferred directly to the RF coil (the "forward" power), and the amount of power reflected back due to losses in the circuit and mis-tuning (the "reflected" power). Once the tuning state is determined by comparing the values of the forward and reflected powers, the coil is re-tuned by switching capacitance according to a predetermined sequencing as has been discussed above.

When coil 34 is loaded with a package of unknown contents, it becomes de-tuned. In one application of this invention, to re-tune the coil, eight vacuum relays switch the capacitors arranged in pF values of powers of two, that is, 10, 20, 40, 80. This particular arrangement is capable of producing 256 values of capacitance for re-tuning the system, with a maximum total of 3000 pF. Rather than overloading the system with one relay for each value of capacitance, this power arrangement minimizes the number of relays needed to produce a given value of capacitance (eg. 10+20=30; 20+80=100, etc.), and affords very fast operational speed. It should be noted that the same algorithm can be used with a continuously-variable capacitance system. A stepper motor could be employed and the actual tuning sequence would be very similar to that described for discrete, direct capacitor tuning. The direct coil tuning capacitance arrangement described above is preferred for this invention.

Using capacitors switched by vacuum relays requires a "settling time" of about 6 ms or less to allow the relays to operate and for the reflected power to achieve a steady-state value. The benefit in overall system ruggedness, efficiency, reliability, and small size due to the fixed switch capacitor scheme overcome any possible advantage in precision tuning which might have been achieved using the more conventional variable capacitors. However, because the system uses switching commands controlled by a computer operated sequence controlling device, it can get exact information on the amount of system de-tuning.

This tuning sub-system offers improved sensitivity for NQR systems by optimum automatic fine tuning of the sample coil (RF coil). Previous developments in coil fine tuning required manual tuning of the system, which is acceptable for the laboratory but undesirable for field use. This system offers the advantage of automatic tuning based on fixed capacitors switched by vacuum relays (designed for high RF switching) rather than bulkier and slower variable capacitors. The proposed system measures changes in coil loading, a feature not available on other detection systems. The system is faster and easier to use than a manually tuned sample coil, and provides information about the state-of-tune of the RF coil which can give an indication of the contents of the coil (the sample). The system also gives the control unit an indication of the performance of the RF amplifier.

Physical configurations of the scanner of the system will be described with respect to FIGS. 2, 3 and 4. RF coil 34 is a hollow rectangular tube of thin sheet conductive material, as previously described, foraged on thin-walled rectangular insulator 51 (See FIG. 3). Shield 37 is a conductor in the shape of a rectangular copper (or other highly conductive material) sleeve enclosing the coil and spaced from it by a distance of about one half the length of the shortest side of the coil. The shortest side of the coil is represented by distance "X" in FIG. 3 and the spacing is preferably X/2. As an example of actual size, X is five to six inches, so the spacing between coil 34 and shield 37 would be about 2.5 to 3.0 inches. Another significant measurement is the distance between the edge of coil 34 and opening 52 through which the item to be tested is inserted. That is the same X/2 distance, or about 2.5–3.0 inches. The RF shield provides the coil and probe units, that is, the structure within the RF shield, with the necessary EMI/RFI (electromagnetic interference/radio frequency interference) shielding from external noise. At the same time, the structure inhibits RFI from escaping from the specimen testing cavity. This configuration has been optimized to provide the best balance between noise isolation of the coil, loading of the coil, and minimization of the total system volume.

Figure 3:
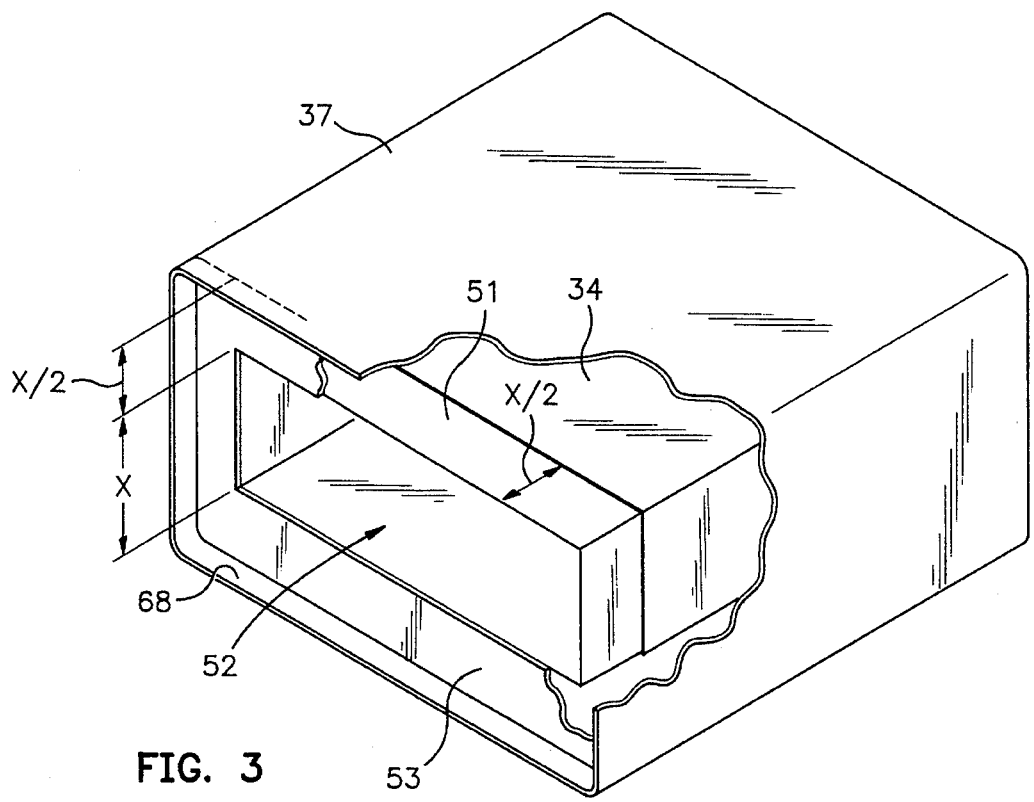
FIG. 3 is a partially cut away perspective view of the scanner portion of the FIG. 2 device.

To complete the dimensions of the scanner of FIG. 3 for purposes of example, the long dimension of the rectangular cavity at the opening may be 16 inches, and the length of the cavity within the coil may be 24 inches. Surrounding shield 37 may have a depth of 10–11.5 inches, a width of about 20–22 inches, and a front-to-back length of at least about 27 inches. The volume of the cavity would be about 2000 in$^3$ (26 liters). The scanner described above may be referred to as a box with a cavity therein, having external access opening 52 to the cavity.

Different arrangements are necessary for the front and back of the coil. The best RFI shielding is normally an electrically connected and grounded box that completely encloses the RF coil, such that external noise cannot reach the RF coil directly. For most real-world applications of this technology, this arrangement is not always possible. An RFI trap or cutoff device is needed to permit access to one or both ends of the coil for movement of the sample item in and out of the coil. In an application of this invention, a portable hand-fed mail or package scanning device, only one end is open and this end, door 85, (FIG. 2) is closed after the package is inserted and before the test is commenced. This closed configuration completes the RFI trap.

Figure 4:
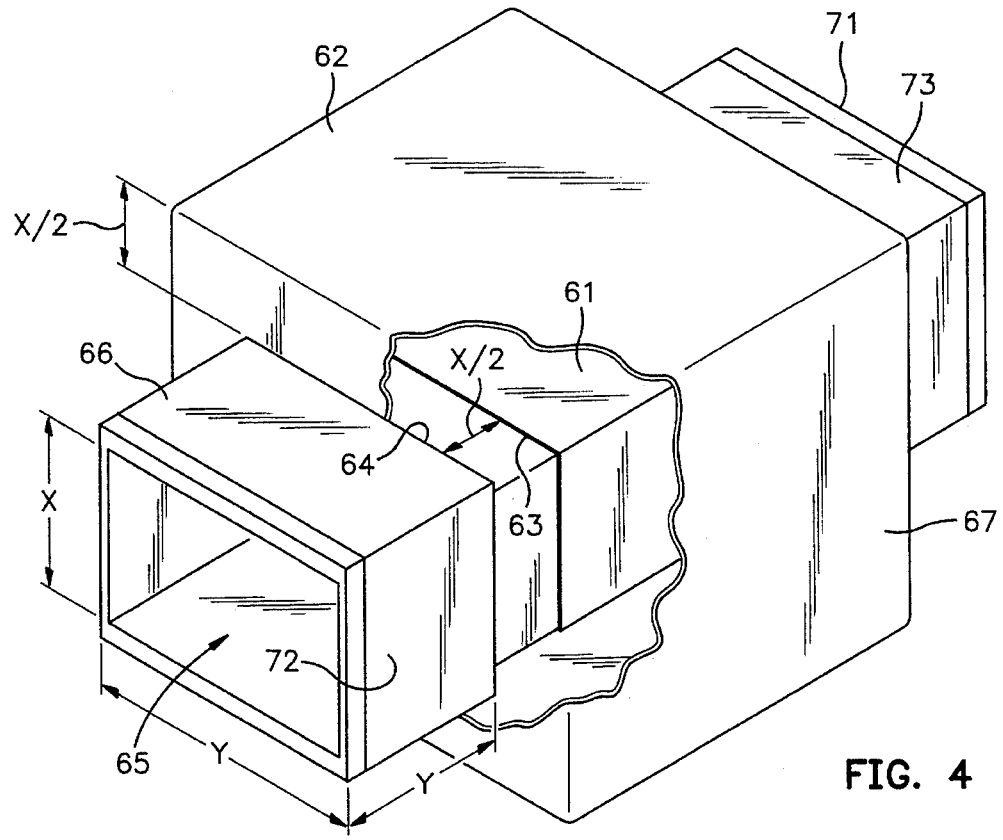
FIG. 4 is a partially cut away perspective view of a baggage inspection device constructed according to the invention.

For a conveyor system to scan airline baggage, both ends of the RF shield are, of necessity, open, as shown in FIG. 4. To provide the necessary RFI shielding, a tunnel, commonly known as a "wave guide below cut-off" of about the same maximum cross-sectional dimension as the coil, is required. Ends 66 and 71 provide the wave guide below cut-off for this configuration of the invention. While the overall dimensions are greater, the coil, shield and opening relationships remain substantially consistent. In this case the "X" dimension between coil 61 and shield 62 is X/2, the same as between edge 63 of the coil and end 64 of the main part of baggage-size scanner structure 67. As an example, the X dimension may be 18 inches and the width, dimension "Y," could be around 28 inches. Opening 65 is the same size all the way through wave guide or tunnel end extension 66, the main tunnel (not shown) through test apparatus box 67, and out through wave guide or tunnel end extension 71.

Some additional exemplary dimensions are given here for purposes of completeness. The front-to-back length of the cavity, in scanner box 67, is about 36 inches and the cavity volume would be about 10.5 ft$^3$ (305 liters).

While X/2 is the preferred spacing discussed above, it need not have exactly that relationship to the short dimension of the coil cavity. The shield spacings may range between X/3 and X, with X/2 being preferred at the present time.

In addition to the coil and shield, some typical materials for facing 53 and for the inner rectangular frame are wood and plastic. They should be relatively light, rigid, and be an electrical insulator. In the larger, double open-ended version of FIG. 4, external surfaces 72 and 73 of tunnel ends 66 and 71 would likely be copper or aluminum, while the inside and facing would be plastic or wood.

Figure 2:
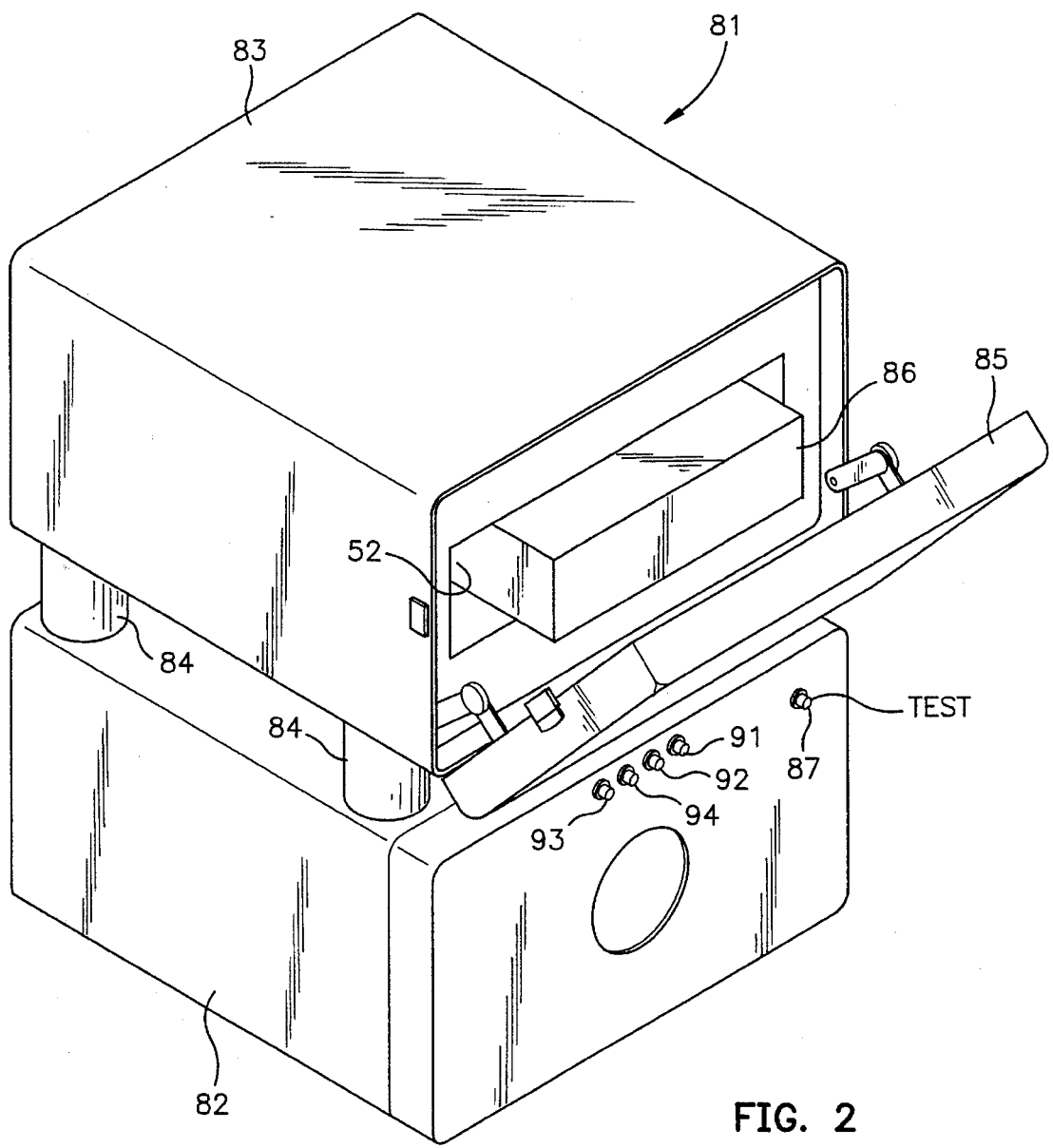
FIG. 2 is perspective view of an actual device in accordance with the invention for small package inspection incorporating the FIG. 1 system therein.

A practical smaller size, or portable, mail scanner 81 is shown in FIG. 2. The electronics and control functional elements can be contained in box 82. The scanning device itself is box 83 mounted on top of box 82 by stand-offs 84. The front of scanner 83 is normally closed by front door or lid 85 which is hinged to the top box. A package 86 is shown in opening 52, within the RF coil, ready for test.

To reiterate, in the portable mail scanner of FIGS. 2 and 3, only one end of the coil is required to be open for access to the coil compartment or cavity. The shield entirely surrounds the coil, except for an opening of the same cross-sectional area as the coil. This opening forms a slot through which packages can be passed. The opening in the detects that an excessive amount of re-tuning of the coil is necessary, compared to an average investigation or predefined threshold, or an acoustic ringing signal is detected, the condition is flagged and yellow warning light 94 illuminates. The yellow warning light indicates that: (1) there is an abnormally high amount of metal in the coil, (2) a high quantity of high dielectric material is detected, or (3) a spurious acoustic signal has been detected. Further alternative testing or visual inspection can be used to resolve inconclusive results of the NQR test.

In addition to the illumination indications mentioned above, the display device can optionally provide graphical display 95 of the signal showing both the in-phase and quadrature signals, as well as other signal and system characteristics. Also optionally, printed output 96, including the time, date, signal amplitude and frequency, as well as coil tuning parameters, and other information such as acoustic signal responses from speaker 97, can be provided.

The factors which have degraded the effectiveness of previous NQR signal detectors are reduced or eliminated by this system. If conductive or high dielectric materials are present in the sample, the auto-tune sub-system will be employed in an attempt to neutralize the effect of the foreign material. Then visual inspection can be accomplished if there is reason to do so. The auto-tune capability can quickly account for changes in temperature which affects tuning capacitance, as well as movement or distortion of the coil which might occur when samples are put into the cavity.

Examples of two embodiments of the invention have been described above. It is likely that modifications and improvements will occur to those skilled in this technical field which are within the scope of the appended claims.

What is claimed is:

1. A system for detecting a target substance within a class of explosives and narcotics containing quadrupolar nuclei in a specimen employing the phenomenon of nuclear quadrupole resonance (NQR), said system comprising:

a sequence controller having means for providing timing and programming pulses to said system;

a radio frequency (RF) subsystem comprising a variable frequency RF source to provide pulsed RF excitation at a frequency generally corresponding to predetermined characteristic nuclear quadrupolar resonant frequency of the specimen, wherein nuclear quadrupolar resonant frequency is the frequency of nuclear precession due to quadrupolar interaction with molecular electric field gradients;

a detection head subsystem comprising:

a single turn distributed RF coil sheet shaped and configured to define a cavity of predetermined volume therein and to receive the specimen within the cavity defined by said RF coil, said cavity having a first end and a second end, the RF signal from said RF source being transmitted within said cavity and being uniformly applied to the specimen within said RF coil cavity and generating a uniform field within said cavity, said RF coil also functioning as the pickup coil for the NQR signals from the specimen and providing an NQR output signal;

apparatus for tuning said RF coil to about the desired characteristic nuclear quadrupolar resonant frequency for the specimen under test; and an electrically conductive RF shield surrounding and spaced from and electrically isolated from said RF coil, said RF shield being shaped and configured to provide electromagnetic interference and radio frequency interference (EMI/RFI) shielding from external noise and to prevent RF and magnetic flux from escaping from said RF coil cavity and RF shield combination, said RF shield configuration being longer than said RF coil, thereby extending beyond both said first end and said second end of said coil, said RF shield being an electrically integral part of said RF coil to improve the Q and the efficiency of said RF coil and contributing to the uniformity of flux field applied to the specimen within said RF coil, said RF coil and RF shield together forming a scanner;

a signal capture and data processing subsystem having a digital signal processor and comprising:

means for receiving the NQR output signal from said RF coil;

memory means storing characteristics of NQR signals from at least one target substance in the class explosives and narcotic compounds;

means for processing the NQR output signal from said RF coil; and means for comparing characteristics of the processed NQR output signal with the characteristics in memory and emitting a final output signal; and a display device receiving the final output signal from said signal capture and data processing subsystem and, in response thereto, said display device selectively indicating the presence of the target substance, the absence of the target substance, and an intermediate result when conditions of the received signal from the specimen indicate that further testing is necessary.

2. The system recited in claim 1, wherein said RF coil cavity is configured to leave at least one end accessible, through which the specimen can be inserted.

3. The system recited in claim 2, wherein both ends of said cavity are open to enable specimens to enter at one end and leave at the other end in a continuous manner.

4. The system recited in claim 1, wherein said cavity is rectangular in shape, with its shorter sides having a first dimension, the spacing between said RF coil and said RF shield being in the range of about one-third of said first dimension to the full length of said first dimension.

5. The system recited in claim 4, wherein the spacing between said RF coil and said RF shield is about one-half of said first dimension.

6. The system recited in claim 4, wherein said RF shield extends past at least the open end of said RF coil by a distance that is substantially equal to one-half of said first dimension.

7. The system recited in claim 1, and further comprising at least one cavity extension element coupled to said scanner and comprising a wave guide below cut-off, said extension element having an opening therethrough which is the same size as said cavity.

8. The system recited in claim 1, and further comprising a cavity extension element coupled to each end of said scanner and having an opening therethrough which are the same size as said cavity, said extension elements comprising wave guides below cut-off.

9. The system recited in claim 1, wherein said cavity is rectangular in shape, with its shorter sides having a first dimension, the spacing between said RF coil and said RF shield being in the range of about one-third of said first dimension to the full length of said first dimension.

10. The system recited in claim 9, wherein said RF shield extends past at least the open end of said RF coil by a distance that is substantially equal to one-half of said first dimension.

11. The system recited in claim 1, wherein said tuning apparatus comprises means for automatically tuning said RF coil after the specimen is inserted therein for maximum power transfer efficiency.

12. The system recited in claim 11, wherein said automatic tuning means comprises:

a series of fixed value capacitors switched by controllable switch means; and control means for controlling the switching sequence of said capacitors to establish maximum power transfer efficiency of said RF coil.

13. The system recited in claim 12, wherein each successive capacitor has a capacitive value which is a power of two greater than the previous one.

14. The system recited in claim 12, wherein said controllable switch means comprise a series of vacuum relays, one for each said capacitor, said vacuum relays being individually controlled by said control means.

15. The system recited in claim 1, and further comprising means to identify and differentiate acoustic ringing signals from NQR signals.

16. The system recited in claim 15, wherein said identifying and differentiating means comprises said sequence controller and said RF source, in combination with said detection head subsystem to apply excitation RF pulses to said RF coil which are separate and distinct from the RF excitation pulses at the quadrupolar resonant frequency.

17. A method for detecting a target substance within a class of explosives and narcotics containing quadrupolar nuclei in a specimen, said method employing the phenomenon of nuclear quadrupole resonance (NQR) in a detection system and comprising the steps of:

forming a scanner comprised of a single turn distributed RF coil sheet shaped and configured to define a cavity of predetermined volume therein and to receive the specimen within the cavity defined by the RF coil, the RF coil being surrounded by an electrically conductive RF shield which is spaced from and electrically isolated from the RF coil, the shield being shaped and configured to provide electromagnetic interference and radio frequency interference (EMI/RFI) shielding from external noise and to prevent RF and magnetic flux from escaping from the scanner, the RF shield configuration being longer than the RF coil, thereby extending beyond the ends of the RF coil, the RF coil and RF shield being an integral combination portion of the scanner and being designed to improve the Q and the efficiency of the RF coil, the RF coil and RF shield contributing to the uniformity of flux field applied to the specimen when it is inserted within the RF coil cavity;

entering known characteristics of NQR signals of target substances in memory in a data signal processor in the detection system;

providing precisely programmed timing pulses to the detection system;

inserting the specimen within the cavity formed in the RF coil; then automatically tuning the RF coil to maximum power transfer efficiency for RF signals transmitted within the RF coil cavity;

providing excitation RF pulses of a predetermined frequency to the RF coil;

transmitting the RF pulses into the cavity formed by the RF coil and creating a uniform flux field within the RF coil to which the specimen is subjected;

detecting by the RF coil the NQR signals emitted by target substances within the specimen;

processing the NQR signals and comparing them to signal characteristics in memory to determine whether the detected NQR signals indicate the presence of a target substance; and selectively indicating whether the target substance is present in the specimen, whether the target substance is absent frown the specimen, and whether conditions of the received signal indicate that further examination is necessary.

18. The method of claim 17, and comprising the further step of identifying acoustic ringing signals and differentiating said ringing signals from NQR signals.

19. The method recited in claim 18, wherein said identifying and differentiating step comprises the steps of applying an RF signal to the RF coil which is separate and distinct from the NQR excitation signal, and determining if a ringing signal is present.

* * * * *